US006372923B1

(12) United States Patent
Uno et al.

(10) Patent No.: US 6,372,923 B1
(45) Date of Patent: Apr. 16, 2002

(54) PROCESS FOR PREPARING ALCOHOL DERIVATIVES

(75) Inventors: Mitsuru Uno; Munehisa Okutsu; Tomohito Kitsuki, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/583,777

(22) Filed: May 31, 2000

(30) Foreign Application Priority Data

Jun. 1, 1999 (JP) .......................................... 11-153850

(51) Int. Cl.⁷ ...................... C07D 301/28; C07C 43/11; C07C 69/708; C07C 43/04
(52) U.S. Cl. ...................... 549/516; 560/183; 560/184; 560/187; 560/209; 568/608; 568/614; 568/618; 568/621
(58) Field of Search ................................ 560/183, 184, 560/187, 209, 233; 568/608, 614, 618, 621; 549/516

(56) References Cited

U.S. PATENT DOCUMENTS

| 4,721,816 A | 1/1988 | Edwards |
| 4,825,009 A | 4/1989 | Edwards |

FOREIGN PATENT DOCUMENTS

| DE | 1 937 728 | * | 2/1970 |
| EP | 0 980 869 | | 2/2000 |
| JP | 62-164641 | | 7/1987 |
| WO | WO 98/50389 | | 11/1998 |

* cited by examiner

*Primary Examiner*—T. A Solola
(74) *Attorney, Agent, or Firm*—Oblon, Spivak, McClelland, Maier & Neustadt, P.C.

(57) ABSTRACT

The present invention provides a process for preparing an alcohol derivative, where the alcohol derivative is an ester, acetal, ketal, ether glycoside, or alkyl glycoside, by reacting an alcohol with a carbonyl compound, alcohol, olefin, epoxy compound or saccharide, where $C_{2-4}$ vicinal alkylene oxides are excluded, in the presence of (A) an aluminum alkoxide and (B) sulfuric acid or phosphoric acid.

14 Claims, No Drawings

PROCESS FOR PREPARING ALCOHOL DERIVATIVES

FIELD OF THE INVENTION

The present invention relates to a process for preparing an ester, acetal, ketal, ether or alkyl glycoside in the presence of an aluminum catalyst.

BACKGROUND OF THE INVENTION

To prepare a glycidyl ether, two processes have conventionally been known. The first is one-stage process where an alcohol and an α-epihalohydrin are reacted in the presence of an alkali and a phase transfer catalyst such as a quaternary ammonium salt. The second is a two-stage process where an alcohol is reacted with an α-epihalohydrin in the presence of an acid catalyst and the resulting halohydrin ether is subjected to ring closure with an alkali. In the one-step process, an excess amount of the α-epihalohydrin is required to prevent further addition of the alcohol to the resulting glycidyl ether. In the two-step process, the alcohol must be added in an excess amount relative to the α-epihalohydrin, because the conversion ratio of the alcohol is not high enough in the presence of a bronsted acid catalyst, e.g., sulfuric acid. Furthermore, excessive addition reactions of the α-epihalohydrin to the halohydrin ether occurs when a highly active Lewis acid such as boron trifluoride or tin tetrachloride is used as an acid catalyst. Metal chloride such as aluminum chloride, tin chloride or iron chloride used as a Lewis acid catalyst are problematic because of catalyst deactivation by alcoholysis and the reaction of free chlorine with the α-epihalohydrin. Moreover, in the two-stage process a hydrophilic solvent or phase transfer catalyst must be used in order to efficiently close the halohydrin ether ring with an alkali.

Examples of preparing dialkylglyceryl ether are a process of reacting an alcohol with an α-epihalohydrin in the presence of an alkali and a process of reacting glycerin with an alkyl halide in the presence of an alkali. However, these reactions require alcohol or an alkyl halide to be used in large excess which is problematic because simultaneous introduction of two different alkyl groups is considerably difficult. Although it is possible to obtain a dialkylglyceryl ether containing freely selected alkyl groups if an alcohol and a glycidyl ether are reacted in the presence of an alkali or acid catalyst, using alkali is problematic because an excess alcohol must be used to prevent further reaction of the product whereby the glycidyl ether partially undergoes hydrolysis. Using an acid is also problematic because the glycidyl ether is polymerized during the reaction.

A process for preparing an ester, acetal, ketal, ether or alkyl glycoside by using, as a catalyst, a combination of an aluminum alkoxide and a phenol or sulfonic acid or a compound wherein these two have been bonded is described in WO98/50389. However, the yields obtained by this process were not satisfactory and thus further yield improvements are necessary. Additionally, this process is unsatisfactory because of the significant increase of Chemical Oxygen Demand (COD) in the water layer, thereby burdening waste water disposal.

A process for preparing an alkanol alkoxylate product characterized by a narrow-range alkylene oxide adduct distribution and a low content of a residual alkanol, which comprises reacting an alkylene oxide reactant composed of at least one $C_{2-4}$ vicinal alkylene oxide with an alkanol reactant composed of at least one $C_{6-36}$ alkanol in the presence of a catalytically effective amount of a catalyst, where the catalyst was prepared by contacting (i) at least one sulfur-containing acid and (ii) at least one aluminum compound, e.g., aluminum alcoholates or aluminum phenolates (Japanese Patent Application Laid-open No. SHO 62164641). This process aims to prepare a nonionic surfactant by adding a plurality of moles of a $C_{2-4}$ vicinal alkylene oxide to an alcohol. An ether with only 1 mole of an alkylene oxide is not available by this process.

The present inventors have found that the combination of an aluminum alkoxide and sulfuric acid or phosphoric acid makes it possible to effectively prepare an ester, acetal, ketal, ether or alkyl glycoside and in addition to facilitate waste water disposal without raising the COD in the water layer.

SUMMARY OF THE INVENTION

In accordance with this finding, an object of the present invention is a process for preparing an ester, acetal, ketal, ether or alkyl glycoside, which comprises reacting an alcohol with a carbonyl compound, alcohol, olefin, epoxy compound (except $C_{2-4}$ vicinal alkylene oxide) or saccharide in the presence of (A) an aluminum alkoxide and (B) sulfuric acid or phosphoric acid.

Another object of the present invention is a process for preparing a glyceryl ether, which comprises reacting an alcohol and an α-epihalohydrin in the presence of the above-described catalyst and reacting the ether obtained with an alkali.

Another object of the present invention is a process for preparing a monoalkylglyceryl ether which comprises; hydrolyzing the glycidyl ether thus obtained.

DETAILED DESCRIPTION OF THE INVENTION

The aluminum alkoxide (A) catalyst can be any aluminum alkoxide in the form of a mono-, di- or tri-alkoxide. Among them, an aluminum trialkoxide is more preferred, with an aluminum tri($C_{1-4}$ alkoxide) being particularly preferred. Specific examples of the aluminum alkoxide include aluminum trimethoxide, aluminum triethoxide, aluminum triisopropoxide and aluminum triisobutoxide, with aluminum triisopropoxide being particularly preferred. Commercially available aluminum alkoxides can also be used.

Alternatively, a mixture of mono-, di- and tri-alkoxide forms available by reacting an aluminum trihalide or trialkyl aluminum with an alcohol can be used. In this case, it is preferred to select the conditions permitting the preparation of a mixture having a larger trialkoxide content.

Sulfuric acid or phosphoric acid (B) catalyst efficiently catalyzes the above-described reaction when used in combination with the above-described aluminum alkoxide. The reaction does not proceed in the presence of aluminum sulfate. As the catalyst (B), sulfuric acid is preferred, with concentrated sulfuric acid having a concentration of 90% or greater being more preferred and concentrated sulfuric acid or fuming sulfuric acid having a concentration of 96% or greater being particularly preferred. In the present invention, a combination of aluminum triisopropoxide and sulfuric acid or phosphoric acid is preferred, of which the combination of aluminum triisopropoxide and sulfuric acid is particularly preferred.

Alcohols usable in the present invention include those represented by the following formula (1):

$$R^1\text{—}(OA^1)_m\text{—}OH \tag{1}$$

wherein, $R^1$ represents a saturated or unsaturated, linear or branched hydrocarbon group having 1 to 36 carbon atoms in total, $A^1$ represents a $C_{2-4}$ alkylene group and m is 0 to 100. Specific examples include saturated aliphatic alcohols such as methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, 2-ethylhexanol and 3,5-dimethylhexanol; and unsaturated aliphatic alcohols such as oleyl alcohol and linoleyl alcohol; and alkylene oxide adducts thereof. As such an alkylene oxide adduct, an ethylene oxide adduct (an alcohol of the formula (1) wherein $A^1$ represents ethylene) and the number ((m) in the formula (1)) of moles added is preferably 0 to 20. As alcohols, those free of an alkylene oxide (alcohols of the formula (1) wherein m stands for 0) are preferred.

Examples of the carbonyl compound usable in the present invention include carboxylates, aldehydes and ketones. By the use of, as a raw material, a carboxylate, aldehyde or ketone, the corresponding ester, acetal or ketal can be prepared, respectively. By the reaction of the above-described alcohol with another alcohol, an olefin or an epoxy compound, the corresponding ether can be obtained. Reaction of the above-described alcohol with a saccharide yields the corresponding alkyl glycoside.

Among them, reaction between the alcohol and epoxy compound (except $C_{2-4}$ vicinal alkylene oxides) is particularly preferred in the present invention. As the epoxy compound, α-epihalohydrins such as α-epichlorohydrin, α-epibromohydrin and α-epiiodohydrin and 1,2-epoxy compounds represented by the following formula (2):

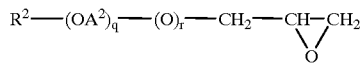

(2)

wherein, $R^2$ represents a hydrogen atom or a saturated or unsaturated, linear or branched $C_{1-24}$ hydrocarbon group which may have a substituent, $A^2$ represents a $C_{2-4}$ alkylene group, q stands for 0 to 100, and r is 0 or 1, with the proviso that $R^2$ represents a $C_{1-24}$ hydrocarbon group when r is 0. Examples of the compound represented by the formula (2) include 1,2-epoxyalkanes such as 1,2,-epoxyhexane, 1,2-epoxyoctane, 1,2-epoxydecane and 1,2-epoxydodecane and alkyl glycidyl ethers such as butyl glycidyl ether, octyl glycidyl ether and dodecyl glycidyl ether and glycidol. Among the epoxy compounds, α-epihalohydrins and glycidol are more preferred.

In the halohydrin-ether forming reaction, the alcohol is preferably added in an amount of 0.5 to 5.0 moles, more preferably 0.5 to 2.0 moles, particularly preferably 0.8 to 1.5 moles per mole of the α-epihalohydrin. The catalyst (A) is preferably added in an amount of 0.001 to 0.1 mole, particularly preferably 0.005 to 0.05 mole per mole of the α-epihalohydrin. When sulfuric acid is employed as the catalyst (B), sulfuric acid is added in an amount of 0.8 to 1.75 moles, more preferably 1.0 to 1.75 moles, particularly preferably 1.25 to 1.5 moles per mole of the catalyst (A). When phosphoric acid is employed as the catalyst (B), phosphoric acid is preferably added in an amount of 0.67 to 1.2 moles, particularly preferably 0.8 to 1.0 time mole per mole of the catalyst (A). The ratio of these catalysts is an important factor in the present reaction. The reaction temperature is 50 to 150° C., with 70 to 130° C. being particularly preferred. The reaction time is preferably 1 to 5 hours.

The raw material ratio, catalyst ratio and reaction temperature in the reaction of the alcohol with the carbonyl compound, alcohol, olefin or saccharide are similar to those in the reaction of the alcohol with the α-epihalohydrin.

It is preferred to charge the alcohol and the catalysts (A) and (B) and after removal of water, react them with the α-epihalohydrin. The water content in the system is preferably 0.2% or less, with 0.1% or less being more preferred. Removal of water from the system suppresses the polymerization of the α-epihalohydrin, whereby a target halohydrin ether can be obtained in a high yield.

From the halohydrin ether obtained by the above-described reaction, the corresponding glycidyl ether can be prepared by adding, to the halohydrin ether, an alkali without removing the catalysts from the reaction mixture and then effecting ring closure by the hydrogen-halide eliminating reaction.

Examples of alkali include hydroxides of alkali metals such as sodium hydroxide and potassium hydroxide and hydroxides of an alkaline earth metal such as calcium hydroxide and barium hydroxide, of which sodium hydroxide and potassium hydroxide are preferred.

In the ring closure reaction of the halohydrin ether, the alkali is preferably added in an amount of 1.0 to 4.0 moles per mole of the amount of the α-eihalohydrin charged, particularly preferred is 1.0 to 2.0 moles per mole of the amount of the α-eihalohydrin charged. For example, it is preferred to add the alkali in the form of a 10 to 50% aqueous solution. The reaction is preferably carried out at 40 to 110° C. for 0.5 to 8 hours.

The glycidyl ether thus obtained can he converted into the corresponding monoalkyl glyceryl ether by hydrolysis in a conventional manner. Examples of hydrolysis are disclosed in Japanese patent application laid-open No. 49-86307, wherein hydrolysis of glycidyl ether is carried out in an aqueous solution of aliphatic acid mono or polycarboxylic acid salt, and Japanese patent application laid-open No. 56-133281, wherein a carbonyl compound is added to a glycidyl ether to give a 1,3-dioxolan compound, this compound being subsequently hydrolyzed.

When the compound represented by the formula (2) is employed as the epoxy compound, ethers represented by the following formula (3):

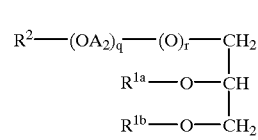

(3)

wherein $R^2, A^2$, q and r have the same meanings as described above, and one of $R^{1a}$ and $R^{1b}$ represents a hydrogen atom while the other one represents $R^1$—$(OA^1)_m$— in which $R^1$, $A^1$ and m have the same meanings as described above can be obtained.

The target compounds, for example, glycidyl ethers and alkyl glyceryl ethers, can be isolated and purified by known isolation and purification means, more specifically, distillation, recrystallization or column chromatography.

Having generally described this invention, a further understanding can be obtained by reference to certain specific examples which are provided herein for purposes of illustration only, and are not intended to be limiting unless otherwise specified.

EXAMPLES

Example 1

Amyl alcohol (660.2 g, 7.5 mole), 5.11 q of aluminum triisopropoxide (0.025 mole) and 3.35 g of 96% sulfuric acid (0.033 mole) were heated to 90° C. while stirring under a nitrogen gas atmosphere. To the reaction mixture, 462.5 g (5.0 mole) of epichlorohydrin was added dropwise over 1 hour, followed by stirring for 3 hours. It was found that the conversion ratio of the raw material epichlorohydrin was 100%, while the yield of the resulting halohydrin ether was 95%. To the reaction mixture, 1270 mL of a 4N aqueous solution of sodium hydroxide was added and the resulting mixture was stirred at 60° C. for 6 hours. After cooling to room temperature, the water layer was removed and the residue was purified by distillation under reduced pressure, whereby 657 g of amyl glycidyl ether (1,2-epoxy-4-oxanonane) was obtained (total yield: 94%).

Example 2

Octanol (195 g, 1.5 mole), 1.02 g (0.005 mole) of aluminum triisopropoxide and 0.7 g (0.007 mole) of 98% sulfuric acid were heated to 90° C. while stirring under a nitrogen gas atmosphere. To the reaction mixture, 92.5 g (1.0 mole) of epichlorohydrin was then added dropwise over 1 hour, followed by stirring for 4 hours. It was found that the conversion ratio of the raw material epichlorohydrin was 100%, while the yield of the resulting halohydrin ether was 95%. To the reaction mixture, 300 mL of a 4N aqueous solution of sodium hydroxide was added and the resulting mixture was stirred at 60° C. for 6 hours. After cooling to room temperature, the water layer was removed and the residue was purified by distillation under reduced pressure, whereby 175 g of octyl glycidyl ether (1,2-epoxy-4-oxadodecane) was obtained (total yield: 95%.).

Example 3

In a four-necked 300-ml flask, 132.0 g (1.5 mole) of amyl alcohol, 1.024 g (0.005 mole) of aluminum triisopropoxide and 0.491 (0.005 mole) of 85% phosphoric acid were charged. While stirring under a nitrogen gas atmosphere, the resulting mixture was heated to 90° C. To the resulting mixture, 92.52 g (1.0 mole) of epichlorohydrin was added over 1 hour, followed by stirring for 4 hours. It was found that the conversion rate of the raw material epichlorohydrin was 100%, while the yield of the resulting halohydrin ether was 92%. To the reaction mixture, 275 mL of a 4N aqueous solution of sodium hydroxide was added and the resulting mixture was stirred at 60° C. for 6 hours. After cooling to room temperature, the water layer was removed and the residue was purified by distillation under reduced pressure, whereby 131 g of amyl glycidyl ether (1,2-epoxy-4-oxanonane was obtained (total yield: 91%).

Comparative Example 1

Amyl alcohol (132 g, 1.5 mole), 1.02 g (0.005 mole) of aluminum triisopropoxide and 2.64 g (0.015 mole) of p-phenolsulfonic acid were heated to 90° C. while stirring under a nitrogen gas atmosphere. To the reaction mixture, 92.5 g (1.0 mole) of epichlorohydrin was added dropwise over 1 hour, followed by stirring for 4 hours. It was found that the conversion ratio of the raw material epichlorohydrin was 100%, while the yield of the resulting halohydrin ether was 87%. To the reaction mixture, 300 mL of a 4N aqueous solution of sodium hydroxide was added and the resulting mixture was stirred at 60° C. for 6 hours. After cooling to room temperature, the water layer was removed and the residue was purified by distillation under reduced pressure, whereby 124 g of amyl glycidyl ether (1,2-epoxy-4-oxanonane) was obtained (total yield: 86%).

Comparative Example 2

In a four-necked 300-ml flask, 132 g (1.5 mole) of amyl alcohol and 3.16 g of aluminum sulfate were charged, followed by heating to 90° C. while stirring under a nitrogen gas atmosphere. To the resulting mixture, 92.5 g (1.0 mole) of epichlorohydrin was then added dropwise over 1 hour and the resulting mixture was stirred for 6 hours as it was. It was found that the conversion ratio of the raw material epichlorohydrin was 15%, while the yield of the resulting halohydrin ether was 10%.

The yield and COD in the water layer in the above-described Examples and Comparative Examples are shown in Table 1.

TABLE 1

| | Alcohol | Catalyst | Yield of glycidyl ether (%) | COD in water layer (mg/L) |
|---|---|---|---|---|
| Example 1 | Amyl alcohol | (A) Aluminum triisopropoxide (B) Sulfuric Acid | 94 | 2000 |
| Example 2 | Octanol | (A) Aluminum triisopropoxide (B) Sulfuric Acid | 95 | 1200 |
| Example 3 | Amyl alcohol | (A) Aluminum triisopropoxide (B) Phosphoric acid | 91 | 2200 |
| Comparative Example 1 | Amyl alcohol | Aluminum sulfate | 86 | 19,000 |
| Comparative Example 2 | Amyl alcohol | | 10 (Yield of halohydrin ether) | — |

The results of these examples show that a glycidyl ether can be obtained in a high yield according to the present invention. Additionally, in Examples 1 to 3, the COD in waste water was about one-tenth of that in Comparative Example 1, which facilitated waste water disposal.

Example 4

In a four-necked 300-ml flask, 100 g (0.69 mole) of amyl glycidyl ether obtained in Example 1, 25 g (1.39 mole) of water, 2.31 g (0.028 mole) of 48% sodium hydroxide and 5.54 g (0.028 mole) of lauric acid were charged, followed by heating to 90° C. while stirring under a nitrogen gas atmosphere. The stirring was continued for 8 hours. After excess water was distilled off, the residue was distilled under reduced pressure (100° C., 0.133 kPa), whereby 110 g (0.59 mole) of amyl glyceryl ether was obtained (yield: 86%, purity: 99%).

INDUSTRIAL APPLICABILITY

The process of the present invention, a halohydrin ether, acetal, ketal, ether or alkyl glycoside can be obtained in a notably high yield from an alcohol and an α-epihalohydrin, carbonyl compound, alcohol, olefin or saccharide. When a halohydrin ether is obtained, the subsequent ring closure reaction by an alkali proceeds smoothly, whereby a glycidyl ether can be prepared in a high yield. By the hydrolysis of the glycidyl ether, a monoalkyl glyceryl ether can be prepared in a high yield. Moreover, COD in the waste water does not show an increase and thus waste water disposal can be carried out easily. Thus, the process of the present invention is industrially advantageous.

Obviously, numerous modifications and variations on the present invention are possible in light of the above teachings. It is therefore to be understood that within the scope of the appended claims, the invention may be practiced otherwise than as specifically described herein.

The Japanese priority document JP 11-153850 is hereby incorporated, in its entirety, by reference.

What is claimed is:

1. A process for preparing an alcohol derivative which comprises;

reacting an alcohol with an α-epihalohydrin or 1,2-epoxy compound represented by the following formula (2):

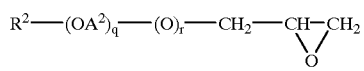

(2)

wherein, $R^2$ represents a hydrogen atom or a substituted or unsubstituted saturated or unsaturated, linear or branched $C_{1-24}$ aliphatic hydrocarbon group, $A^2$ represents a $C_{2-4}$ alkylene group, q is 0 to 100, and r is 0 or 1, with the proviso that $R^2$ represents a $C_{2-24}$ aliphatic hydrocarbon group when r is 0, in the presence of (A) an aluminum alkoxide and (B) sulfuric acid or phosphoric acid, wherein said alcohol derivative is an ether having one molar epoxide adduct, wherein a ratio of sulfuric acid to aluminum alkoxide is 1.25 to 1.5:1.

2. The process of claim 1, wherein the alcohol is in an amount of 0.5 to 5.0 moles per mole of epoxy compound.

3. The process of claim 1, wherein said aluminum alkoxide is selected from the group consisting of aluminum trimethoxide, aluminum triethoxide, aluminum triisopropoxide and aluminum triisobutoxide.

4. The process of claim 1, wherein (B) is sulfuric acid.

5. The process of claim 1, wherein (B) is phosphoric acid.

6. The process of claim 5, wherein the phosphoric acid is present in an amount of 0.67 to 1.2 moles per mole of (A).

7. The process of claim 1, wherein (A) is aluminum triisopropoxide and (B) is sulfuric acid.

8. The process of claim 1, wherein said alcohol is selected from the group consisting of methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, 2-ethylhexanol, 3,5-dimethylhexanol, oleyl alcohol and linoleyl alcohol; and alkylene oxide adducts thereof.

9. The process of claim 1, wherein said epoxy compound is selected from the group consisting of α-epichlorohydrin, α-epibromohydrin, α-epiiodohydrin 1,2,-epoxyhexane, 1,2-epoxyoctane, 1,2-epoxydecane, 1,2-epoxydodecane, butyl glycidyl ether, octyl glycidyl ether and dodecyl glycidyl ether and glycidol.

10. The process of claim 1, wherein said ether is one of the following formula (3)

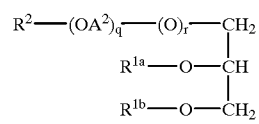

(3)

wherein $R^2$, $A^2$, q and r have the same meanings as described in claim 2, and one of $R^{1a}$ and $R^{1b}$ represents a hydrogen atom while the other one represents $R^1$—$(OA^1)_m$— in which $R^1$ represents a saturated or unsaturated, linear or branched aliphatic hydrocarbon group having 1 to 36 carbon atoms in total, $A^1$ represents a $C_{2-4}$ alkylene group and m is 0 to 100.

11. The process of claim 1, wherein said alcohol derivative is a glycidyl ether and said process comprises reacting an alcohol with an α-epihalohydrin to form an ether and reacting the resulting ether with an alkali.

12. The process of claim 11, wherein said alkali is an alkali metal hydroxide or an alkaline earth metal hydroxide.

13. The process of claim 11, wherein said alkali is present in an amount of 1.0 to 4.0 moles per mole of α-epihalohydrin.

14. The process of claim 11, wherein said process further comprises hydrolyzing the glycidyl ether to obtain monoalkyl glyceryl ether.

* * * * *